United States Patent [19]

Griffin

[11] 4,177,806
[45] Dec. 11, 1979

[54] KNEE PILLOW

[76] Inventor: Teaford A. Griffin, 105 Shearwater Dr., Ocean Springs, Miss. 39564

[21] Appl. No.: 850,281

[22] Filed: Nov. 9, 1977

[51] Int. Cl.² .............................................. A61F 5/30
[52] U.S. Cl. ..................................... 128/132 R; 2/22; 5/238
[58] Field of Search ................. 128/80 C, 132 R, 112, 128/149; 2/24, 65, 16, 22, 239, 241; 5/337, 338, 327 R, 327 H

[56] References Cited

U.S. PATENT DOCUMENTS

| 1,896,561 | 2/1933 | Ruth | 2/24 |
| 3,346,877 | 10/1967 | Zirves | 2/24 |
| 3,465,365 | 9/1969 | Jones et al. | 2/24 |
| 3,604,023 | 9/1971 | Lynch | 5/338 |
| 4,041,940 | 8/1977 | Frankel | 128/80 C |

FOREIGN PATENT DOCUMENTS 794292 12/1935 France .................................. 128/80 C Primary Examiner—Robert W. Michell
Assistant Examiner—Milford Juten
Attorney, Agent, or Firm—Clarence A. O'Brien; Harvey B. Jacobson

[57] ABSTRACT

A knee pillow having a resilient pad forming a surface contoured by formation of an indentation to conform to the knee area of a leg of a person wearing the pillow, and including straps attached to the pad for removably securing the pad to the inside portion of a wearer's leg and preventing the knees of the wearer's leg from digging into one another.

1 Claim, 3 Drawing Figures

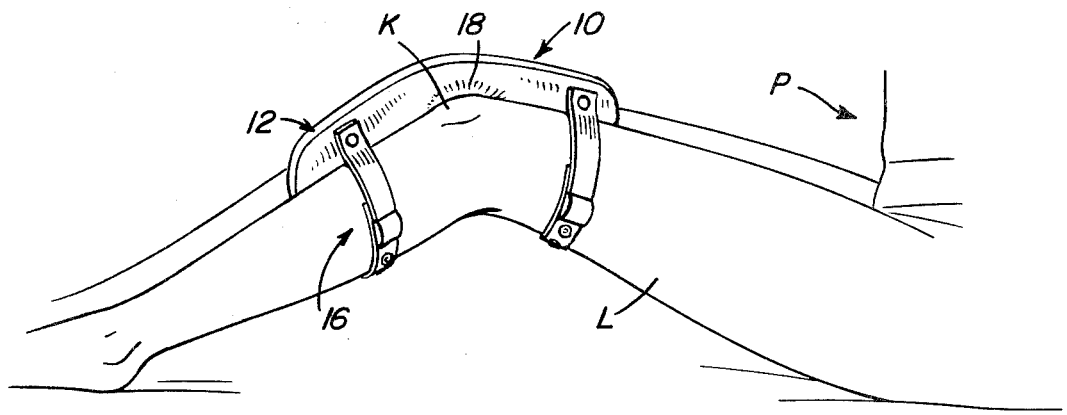
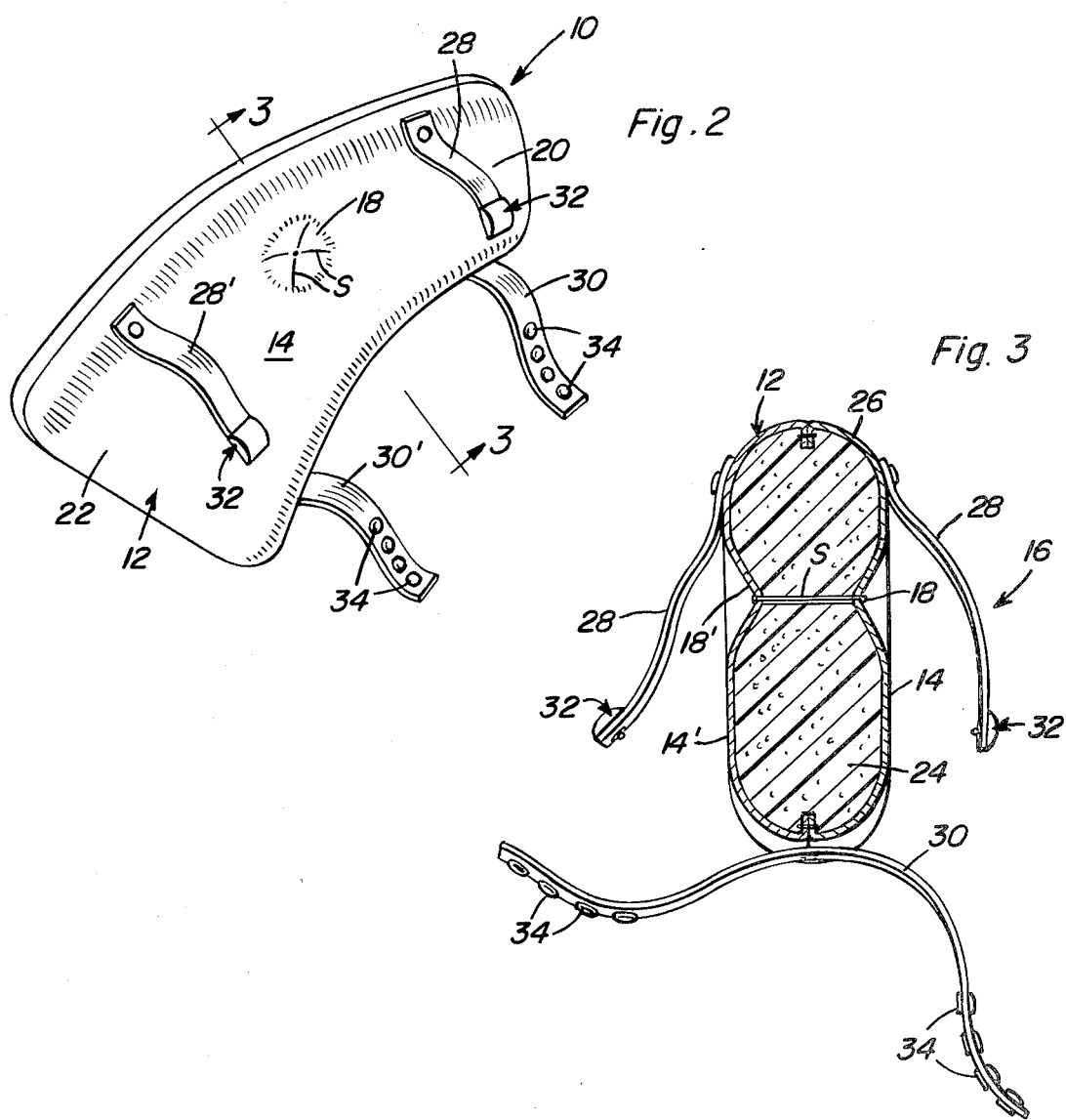

KNEE PILLOW

BACKGROUND OF THE INVENTION

1. Field of the Invention

This invention relates generally to resilient pads or cushions, and particularly to a pad or cushion capable of being secured to the inside portion of the knee area of a wearer's leg in order to protect the knee area from injury.

2. Description of the Prior Art

A substantial segment of the population, particularly the age group 55 and over and persons who suffer from some form of arthritic condition in the lower limbs, require protective padding on the inner portion of the knees in order to prevent digging or gouging of the knees with one another. In particular, it is necessary to provide protective padding in this area which will be effective while the wearer is lying in bed, whether on the back, stomach, or side.

It is generally known to provide knee guards or braces in order to support the joint during violent physical activity, such as football. Examples of such braces can be found in U.S. Pat. Nos. 2,270,685, issued Jan. 20, 1942, to E. Miller, and 2,532,955, issued Dec. 5, 1950, to R. O. S. Shook. These known braces, however, are rather uncomfortable and awkward to wear while sleeping, and the like, and do not necessarily protect the particular inside portion of the knee area required in such circumstances. Further, U.S. Pat. Nos. 1,304,558, issued May 27, 1919, to R. P. Grau; 2,690,747, issued Oct. 5, 1954, to M. E. Frallic; and 3,463,147, issued Aug. 26, 1969, to F. F. Stubbs, disclose body joint protective devices in the form of pads which can be applied to an elbow or knee. These known devices, however, generally cover the entire joint in question, and do not concentrate protection where needed for those persons with the physical problem referred to above, in order to prevent injury and provide relief from pain by concentrating the protection on the inner portion of the knee area of the wearer.

SUMMARY OF THE INVENTION

It is an object of the present invention to provide a resilient pad which can be attached to the inside of the knees of a user while same is sleeping.

It is another object of the present invention to provide a knee pillow or pad which fits on either knee of a user and arrangeable such that when the user lies on either side, for example, the knees thereof will not dig into one another, and such that while lying on one's back or stomach, the pillow will not bulge and distort so as to defeat its purpose.

These and other objects are achieved according to the present invention by providing a knee pillow having: a resilient pad including a surface contoured for conforming to the knee area of a leg of a person wearing the pillow; and an attachment arrangement connected to the pad for removably securing the pad to the leg of a wearer.

According to a preferred construction of the invention, the contoured surface is provided with an indentation arranged for receiving the inner portion of a kneecap of the leg of a wearer, with the indentation being disposed substantially midway of the longitudinal extent of the resilient pad. The contoured surface, or pad itself, extends longitudinally so as to extend from above to below a knee area being protected, and the pad increases in width from one longitudinal end to the other such that the width of the pad, or surface, below the kneecap of a wearer is greater than that above the knee cap.

The attachment arrangement advantageously includes a pair of straps attached to the pad and arranged extending toward one another and provided for cooperating fasteners for being selectively connected together about the leg of a wearer of the device. Preferably, there are two sets of such paid of straps, with such sets of straps being disposed in spaced relation adjacent the longitudinal ends of the pad.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWING

FIG. 1 is a fragmentary, schematic, side elevational view showing a knee pillow according to the present invention attached to the leg of a person.

FIG. 2 is an enlarged, perspective view showing a knee pillow as seen in FIG. 1.

FIG. 3 is an enlarged, sectional view taken generally along the line 3—3 of FIG. 2.

DESCRIPTION OF THE PREFERRED EMBODIMENTS

Referring now more particularly to the figures of the drawing, a knee pillow 10 according to the present invention is formed by a resilient pad 12 including surfaces 14 and 14' contoured for conforming to the knee area K of a leg L of a person P wearing pillow 10. An attachment arrangement 16 is connected to pad 12 for removably securing pad 12 to leg L of person P.

Surfaces 14, 14' of pad 12 are provided with indentations 18, 18' arranged for receiving a kneecap of leg L, with such indentation 18, 18' being disposed substantially midway between a longitudinal extent of pad 12. As can be seen from FIG. 1, pad 12, or the surfaces 14, 14' thereof, increases in width from an end 20 to an end 22 such that the portion of pad 12 below the knee area K has a greater width than that portion of pad 12 above knee area K.

Pad 12 is itself formed from a resilient material 24, such as natural or synthetic foamed rubber, formed in the general over-all configuration of pad 12 and covered by a suitable cloth material 26, which can be fabricated from natural or synthetic fibers. Stitching S is employed as appropriate in the interior portion of pad 12 in order to form the indentations 18 and 18'. This construction not only has the advantage of better fitting on either knee of a user, but will assist in preventing the pad from slipping relative to the kneecap while the wearer is changing positions, and the like.

The attachment arrangement 16 is illustrated as including two sets of cooperating pairs of straps 28, 28' and 30, 30'. Straps 28 extend in opposite directions from end 20 of pad 12, and in the vicinity of the upper edge of the pad 12, while the straps 28' extend in a similar manner from adjacent end 22 of pad 12. The single straps 30, 30' are fastened to the lower edge of pad 12 adjacent the respective ends 20, 22 thereof so as to be associated with the straps 28, 28'. Each of the straps 28, 28' and 30, 30', which may be attached to pad 12 in a suitable manner such as by rivets or stitching to the cover 26, are provided with cooperating fastener parts 32, 34, such a snap-fastener parts, in order to prevent selective fastening together of the straps about the leg L of a wearer of the pillow 10.

While the strap arrangement 16 has been illustrated and described as including identical straps extending from either surfaces 14, 14' of the symmetrical pad 12, it is to be understood that only one set of such straps is required. When constructed as illustrated, however, the pillow 10 can be used on either knee, with the set of straps not being employed being fastened together so as to be placed in a position adjacent the associated one of the surfaces 14, 14' of pad 12.

As can be understood from the above description and from the drawings, a knee pillow according to the present invention provides a suitable pad to be worn while resting or sleeping in order to prevent injury and/or provide relief to the knees of a wearer of the appliance. The specific configuration and construction of the invention permits same to be attached to the inside portion of the knee area of one's leg, or legs, in such a manner as to be extremely comfortable while resisting movement relative to the knee area of the leg. The larger width of the end of the pad which is to be disposed below the knee area permits the pad to conform to the larger width of the calf of the leg on which the appliance is secured.

The foregoing is considered as illustrative only of the principles of the invention. Further, since numerous modifications and changes will readily occur to those skilled in the art, it is not desired to limit the invention to the exact construction and operations shown and described, and accordingly all suitable modifications and equivalents may be resorted to, falling within the scope of the invention.

What is claimed as new is as follows:

1. A pillow for placement between the knees and adjacent upper and lower leg portions of a person lying on his or her side and having their legs disposed in superposed relation, said pillow comprising an elongated resilient pad of greater length than width and of greater width than thickness, approximate longitudinal and transverse midportions of the opposite sides of said pad defining shallow concave recesses opening outwardly from opposite sides of the pad and registered with each other in the direction in which said thickness is measured, said recesses being adapted to seatingly receive the adjacent portions of said person's knees therein with the adjacent knee portions seated in the recesses serving to prevent shifting of the pillow from between the knees and also shifting of the knees from superposed vertically registered positions, the longitudinal extent of said pillow being sufficiently greater than said width to enable the opposite end portions of said elongated pillow to be received between and utilized in maintaining the adjacent upper leg portions and the adjacent lower leg portions of said person comfortably spaced apart, each of said end portions including strap means for adjustable securement about the upper and lower leg portions of one of said legs, said pillow being longitudinally bowed in a plane disposed normal to the direction in which said thickness is measured.

* * * * *